United States Patent [19]
Atwood

[11] Patent Number: 5,766,889
[45] Date of Patent: Jun. 16, 1998

[54] METHOD FOR DETERMINING THE CHARACTERISTICS OF THE CONCENTRATION GROWTH OF TARGET NUCLEIC ACID MOLECULES IN POLYMERASE CHAIN REACTION SAMPLE

[75] Inventor: John G. Atwood, West Redding, Conn.

[73] Assignee: The Perkin-Elmer Corporation, Norwalk, Conn.

[21] Appl. No.: 255,507

[22] Filed: Jun. 8, 1994

[51] Int. Cl.[6] .......................... C07H 21/04; C12P 19/34; C12Q 1/68

[52] U.S. Cl. .......................... 435/91.2; 435/6; 435/91.1; 536/24.33; 536/25.32; 935/77; 935/78

[58] Field of Search .......................... 435/6, 91.1, 91.2; 536/24.33, 25.32; 935/77, 78

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,965,188 | 10/1990 | Mullis et al. | 435/6 |
| 5,219,727 | 6/1993 | Wang et al. | 435/6 |

FOREIGN PATENT DOCUMENTS

0640828  3/1995  European Pat. Off. .

OTHER PUBLICATIONS

Journal of Clinical Chemistry & Clinical Biochemistry, vol. 28, No. 1, 1990 Berlin DE, pp. 5–13, XP 000351816 U.Linz et al. 'Systematic studies on parameters influencing the performance of the polymerase chain reaction'.

(List continued on next page.)

Primary Examiner—Stephanie W. Zitomer
Assistant Examiner—Paul B. Tran
Attorney, Agent, or Firm—Edwin T. Grimes; David Aker

[57] ABSTRACT

Apparatus and method for determining an unknown starting molar concentration of target nucleic acid molecules at the beginning of a polymerase chain reaction in a sample reaction mixture containing suitable buffers, two complementary kinds of oligonucleotide primers, a molar excess of four kinds of nucleoside triphosphates, a DNA polymerase, and the unknown starting molar concentration of target nucleic acid molecules, wherein the two kinds of primers are provided in a known concentration ($C_{po}$), the method including the steps of adding a reporter molecule which does not significantly interfere with the reaction and does not emit a strong signal in the absence of double-stranded DNA, but makes the dsDNA created by the reaction detectable and measurable at least once each cycle, thermal cycling one or more standard reaction mixtures which are substantially the same in every respect except they have known starting molar concentration of target nucleic acid molecules to obtain one or more growth curves with known starting molar concentrations of target nucleic acid molecules, exciting the reaction mixture during at least the extension portion of each cycle, detecting and measuring the intensity of the signal during at least the extension portion of each of the cycles, converting said intensity to molar concentration values of dsDNA and storing the molar concentration values for each of the extension portions of each of the cycles, generating a measured curve of molar concentration of dsDNA versus cycle number from the stored concentration values, using successive approximations, determining values of $e_v$, $e_s$, a, $C_z(n)$ and $A_z(n)$ which provide a best fit of the measured curve to the one or more known growth curves according to the following relation:

$C_{n+1} = C_n e_v$ plus the minimum of $$\left[ \frac{C_n e_v e_s}{1 + \frac{aC_n}{C_{po} + C_o - C_n}} \right] \text{ or } \left[ \frac{C_z(n) A_z(n) t_x}{L_1 - L_p} \right]$$

5 Claims, 4 Drawing Sheets

OTHER PUBLICATIONS

Cabios Computer Applications in the Biosciences, vol. 8, No. 1, 1992 Oxford GB, pp. 65–70, XP 000561190 J. Nedelman et al. 'Quantitative PCR with internal controls'.

Analytical Biochemistry, vol. 214, No. 2, 1 Nov. 1993 Orlando US, pp. 582–585, XP 000413714 L. Raeymaekers 'Quantitative PCR: theoretical considerations with practical implications'.

Higuchi et al. "Kinetic PCR Analysis: Real–time Monitoring of DNA Amplification Reactions." *Bio/Technology*, vol. 11, 1026–1030 (1993).

Wiesner et al., Biochem. Biophys. Res. Comm. 183(2):553–559, 1992.

Wiesner, Nuc. Acids Res. 20(21):5863–5864, 1992.

METHOD FOR DETERMINING THE CHARACTERISTICS OF THE CONCENTRATION GROWTH OF TARGET NUCLEIC ACID MOLECULES IN POLYMERASE CHAIN REACTION SAMPLE

BACKGROUND OF THE INVENTION

1. Field of the Invention

This invention generally relates to biochemical analyses and more specifically to quantitative analysis of nucleic acid samples such as DNA in a polymerase chain reaction (PCR) process.

2. Description of Related Art

Real time monitoring of DNA amplification during the PCR process is described by Higuchi et al, Bio/Technology Vol. 11, pp. 1026–1030. In this article, Higuchi et al describe a quantitative assay for an amplifiable DNA target sequence which correlates the number of temperature cycles required to reach a certain concentration of the target sequence to the amount of target DNA present at the beginning of the PCR process.

By measuring fluorescence of the samples during each cycle of the PCR, it was found that the number of cycles required to achieve a chosen level of fluorescence varied directly with the concentration of amplifiable targets at the beginning of the PCR process. In this assay a CCD camera with a 600 nm long pass filter was directed at an array of wells each containing a reaction mixture. The reaction mixtures included ethidium bromide, a dye that fluoresces strongly at wavelengths around 600 nm when intercalated into double-stranded DNA, but only very weakly when in free solution. The array of mixtures was flooded with UV light at about 302 nm, which excites the ethidium bromide. The array of samples was subjected to alternating denaturation temperatures and annealing/extension temperatures, i.e. thermal cycles, for a sufficient number of cycles to achieve substantial amplification of the targets. The fluorescence intensities were detected by the CCD during the anneal/extension period of each cycle and the camera output was fed to a personal computer for storage and data manipulation. The camera output was essentially a video image taken at the same time during each annealing/extension portion of each cycle.

The data were then fed to a conventional spreadsheet program in the computer for normalization and manipulation of the resulting intensity values for each well. Each of the wells contained a different initial concentration of target nucleic acid molecules. More specifically, the amplifications were initiated with a dilution series of single stranded HIV template DNA. Starting with $10^8$ templates, 10-fold dilutions were made down to $10^2$ templates. HIV-specific primers were used to make a 142 bp PCR product. A significant fixed amount of genomic DNA was also added to each reaction mixture to simulate typical natural samples.

After amplification was completed, it was found that there was a direct correlation between the number of cycles necessary to achieve a given fluorescence intensity and the logarithm of the concentration of the starting nucleic acid targets. When the log of the initial template concentration was plotted against the number of cycles it took to reach a fluorescence level of 190, the result was a straight line. Using a linear regression fit, the correspondence between $10^8$ to $10^3$ starting copies was better than 0.99 ($r^2 > 0.99$). However, below $10^3$ starting copies, the correspondence deviated significantly due to amplification of nonspecific products.

The method used by Higuchi et al to determine starting copies of DNA depended upon the application of human judgment in observing the recorded growth curves for the various PCRs to determine the best fluorescence level at which to measure the cycles, or fractions thereof, to compare the growth curve of a standard with known starting copies. The level of 190 was chosen to be in the middle of a range in which all the growth curves were relatively straight, in transition from upward curving exponential growth to downward curving toward some limit or asymtote. Only the few data points in each growth curve near the chosen fluorescence level contributed to determining the initial copy numbers. Noise in the few individual measurements can cause larger errors in the final determination of unknown starting copies than would occur if a much larger number of measurements over much more of the growth curve were included in the determination, thus averaging their errors and improving the accuracy of the results.

Also, the method used by Higuchi et al relies on the shape of each growth curve to remain the same as that of the standard without determining whether in fact it does, leaving an opportunity for major error in the result. In contrast, the method and apparatus of this invention requires no human intervention or decisions in processing the data, is able to use nearly all the data points on the growth curves, thus averaging their errors and improving the accuracy of the result, and, further, is able, by determining the shape parameters of each growth curve, to determine whether its PCR is the desired one, and in cases where it is known that there are changes with time or cycles in the reaction conditions, such as thermal degradation of enzyme, to detect this by its effect on the growth curve shape parameters and obtain an accurate result in spite of the changed shape of the growth curves.

Current quality control checks on PCR results typically involve running a gel electrophoretic analysis of the PCR products to verify that the amplification product is in fact the desired nucleic acid sequence, or hybridizing the PCR products with a labeled DNA probe with a sequence complementary to one of the desired product strands. Either of these methods are relatively time consuming procedures. There thus remains a need for a simpler method of verifying the specificity of amplification and, in addition, there is a need for an apparatus which can automatically perform such a quality check during the PCR process.

SUMMARY OF THE INVENTION

In this specification, the following definitions of terms will be utilized.

The term PCR means the well known polymerase chain reaction process originally developed by Dr. Kary Mullis of Cetus Corporation and as particularly described by Dr. Mullis and others in U.S. Pat. Nos. 4,683,202; 4,683,195, and 4,965,188 which are incorporated herein by reference in their entirety.

The term "growth curve" means a set of measurements of product DNA (dsDNA), converted to molar concentrations, present at or near the end of the extension portion of each thermal cycle in a polymerase chain reaction (PCR) made of a particular reaction mixture and taken during each cycle of a PCR process.

The term "primer limited PCR" is a PCR process in which the shape of the growth curve is consistent with there always being adequate polymerase enzyme activity to complete the dsDNA product synthesis of all primed single strands formed during the extension portions of the thermal cycles of the PCR and the plateau in the growth curve of newly synthesized DNA at large product concentrations is asymptotic to the initial concentration of the primers, consistent with the plateau's being caused by competition between primers and complementary single strands reducing the probability that primed strands are formed, and finally, by the exhaustion of primers.

An "enzyme limited PCR" means one in which there is inadequate polymerase enzyme activity to complete synthesis of all primed strands within the extension portion of each cycle, so that at high product concentrations, PCR template molar concentration grows each cycle at a rate limited by the number of bases that can be polymerized during the extension portion of the cycle. The molar concentration growth of template per cycle in this case depends on the length of the template in bases.

It is one object of the present invention to provide a method of determining a unique set of characteristics of a particular PCR and the accurate determination of the starting concentration of target nucleic acid molecules in the PCR.

It is another object of the invention to provide a method of accurately determining the starting concentration of target nucleic acid molecules based on observation of fluorescence during each cycle of the PCR process.

It is another object of the invention to provide an automated apparatus for determining the unique set of PCR characteristic parameters for a particular nucleic acid target.

It is another object of the invention to provide an automated apparatus for verifying the specificity of a given PCR without the need for external standards.

In order to accomplish the above and other objectives, the invention provides in one form thereof a new and improved method for determining an unknown starting molar concentration of target nucleic acid molecules at the beginning of a polymerase chain reaction in a sample reaction mixture containing suitable buffers, two complementary kinds of oligonucleotide primers, a molar excess of four kinds of nucleoside triphosphates, a DNA polymerase, and said unknown starting molar concentration of target nucleic acid molecules. The two kinds of primers are provided in a known concentration ($C_{po}$). This method includes the steps of adding to the PCR a reporter molecule which does not significantly interfere with the reaction, but makes the DNA created by the reaction detectable and measurable at least once each cycle. A typical reporter molecule is ethidium bromide, which, when excited with ultraviolet or blue-green light, fluoresces very strongly when intercalated into double-stranded DNA, but only very weakly when free in solution in the reagent system. Other fluorescent intercalating dyes also work in this method. An example is the dye TOPRO. In fact, any DNA detection molecule system can be used which can remain present in the reaction mixture without interfering with it, and permits the DNA created by the reaction to be measured non-destructively. In one form of the invention, the fluorescent intercalating dye, when incorporated into an extension product, generated by said polymerase chain reaction, is capable of emitting a detectable signal when appropriately excited; thermal cycling said reaction mixture for a number of cycles, each including at least denaturing and extension periods, sufficient to establish a desired final concentration of nucleic acid molecules; and exciting said reaction mixture during at least the extension portion of each cycle. This method further includes the steps of detecting and measuring the intensity (I) of the signal during at least the extension portion of each of the cycles; converting the intensity to molar concentration values of dsDNA and storing the molar concentration values for each of the extension portions of each of the cycles; and generating a measured curve of molar concentration of dsDNA versus cycle number from said stored concentration values. Conversion of signal intensity measurements to molar concentrations can be performed by the usual method of replacing the PCR samples with standard solutions of DNA containing all the same materials in the same amounts, except with several known molar concentrations of the dsDNA template ranging from none, the blanks, through the range of concentrations likely to be produced by the PCRs. Then, by subtracting the blank signals from the signals measured on these known photometric standards, creating a working curve relating measured signal corrected for blank background with molar concentration of template dsDNA. It is not necessary to perform PCR to prepare this working curve. Photometric standard solutions with known molar concentrations of DNA are all that is needed.

Next, the growth curve shape parameters $e_s$, $e_v$, and a, for the PCR to be used are determined, if they are not already known by performing the PCR on one or more standard samples having known initial concentrations of template DNA, and recording their PCR growth curves. Now, using the known initial primer concentrations, $C_{po}$, and the known initial template concentrations $C_o$, using a three-variable successive approximation method, determine the values of $e_s$, $e_v$, and a which define a best fit between the measured growth curves and a calculated growth curve according to the following relation:

$$C_{n+1} = C_n e_v \left\{ 1 + e_s / \left( 1 + \frac{aC_n}{C_{po} - (C_n - C_o)} \right) \right\}$$

where:

$C_{n+1}$ and $C_n$ are the DNA template molar concentrations at the end of the n and n+1 cycle extension periods;

$e_v$ is in theory the template's probability of survival to the next cycle;

$e_s$ is in theory the template's probability of being completely synthesized;

$C_o$ is the molar concentration of starting target nucleic acid molecules;

$C_{po}$ is the starting primer molar concentration;

a is in theory the primer/complementary strand competition factor.

Finally, the starting molar concentration of DNA template in the unknown samples is determined by performing the same PCR under the same conditions as for the PCRs on the known standards, and recording the growth curves. Now, using said same relation, enter the values for $e_v$, $e_s$, and a determined on the known standard sample, together with the known initial primer concentration $C_{po}$ in the same relation above, and vary the unknown initial concentration $C_o$, performing a single-variable successive approximation to obtain a best fit between the caluclated theoretical growth curve thus generated and each measured growth curve. The value of $C_o$ which gives the best fit is taken as the result.

One method of determining the best fit between the calculated and measured growth curves is to take the difference between the measured and calculated molar concentrations at each cycle measured, square this difference, and sum the squares of the difference. Then vary the parameters to be determined to minimize the sum of the squares. Any method that gives equivalent results will work.

The quality of the fit between measured and calculated growth curves is measured by how small the average of the squares of the differences can be made. A useful measure is the root mean square error of fit, or RMS error. This is determined by dividing the sum of the squares of the differences by the number of cycles included in the fit, and taking the square root of the result.

A fit in which the RMS error thus determined is about equal to the concentration equivalent noise of the method of measurement used is a fit of the best quality that can be made. Its accuracy is determined largely by the noise of measurement, not by the theoretical accuracy of the algorithm.

The number of cycles which should be run in practising this method should be at least enough to raise the molar concentration of template molecules to a value above the limit of detectability by whatever means is used to measure the template concentration at the end of each cycle, for the samples with the smallest starting concentrations of interest. Larger numbers of cycles than this will give better results, with decreasing benefit of added cycles once the molar concentration of template DNA has ceased to increase significantly in each cycle.

In another form of the invention, there is provided a new and improved automated apparatus for evaluation in real time the expected adequacy of a polymerase chain reaction in a reaction mixture containing suitable buffers, two complementary kinds of oligonucleotide primers, a molar excess of four kinds of nucleoside triphosphates, a DNA polymerase, and an unknown starting molar concentration of target nucleic acid molecules. The two kinds of primers are provided in a known molar concentration ($C_{po}$), and a suitable concentration of at least one kind of reporter molecule which, when intercalated into an extension product generated by the polymerase chain reaction, is capable of emitting a detectable signal when appropriately excited. This apparatus includes a thermal cycler for thermal cycling the reaction mixture for a number of cycles, each including at least denaturing and annealing/extension periods, sufficient to establish a desired final concentration of nucleic acid molecules. A detection system is provided which includes means for exciting the reaction mixture during at least the extension portion of each cycle and means for detecting and measuring the intensity (I) of the signal during at least the extension portion of each of said cycles. A microcomputer is connected to the detection system for receiving signals therefrom and for converting the intensity to molar concentration values of dsDNA in the mixture and storing these molar concentration values for each of the extension portions of each of said cycles. A user interface is connected to the computer and thermal cycler for inputting user instructions and displaying resulting information. The computer includes means for generating a measured curve of molar concentration of dsDNA versus cycle number from said stored concentration values, and means for using successive approximations to determine characteristic parameter values of $e_v$, $e_s$, and a which provide a best fit of the measured curve to a theoretical model curve according to the following relation:

$$C_{n+1} = C_n e_v \left\{ 1 + e_s \left( 1 + \frac{aC_n}{C_{po} - (C_n - C_o)} \right) \right\}$$

where:

$C_{n+1}$ and $C_n$ are the DNA target molar concentrations measured during the nth and n+1th cycle extension periods;

$e_v$ is the target's probability of survival to the next cycle;

$e_s$ is the target's probability of being synthesized;

$C_o$ is the molar concentration of starting target nucleic acid molecules;

$C_{po}$ is the starting primer molar concentration;

a is the primer/complementary strand competition factor.

According to one aspect of the invention, the detection system includes a fluorimeter for detecting fluorescence from the reaction mix during a portion of the anneal\extension portion of each of the cycles.

According to another aspect of the invention, the apparatus further includes a fiber optic coupling connection between the reaction mix in the reaction tube and the fluorimeter.

The formula or equation which uniquely describes the growth curve of double stranded DNA product (dsDNA) during a polymerase chain reaction, once fit to the actual growth curve of dsDNA, can be used to extrapolate to an unknown portion of the curve to determine the dsDNA concentration in that portion. It can also be used to verify the specificity of a given PCR without the use of separate controls. The specificity of the reaction can also be verified, the starting concentration of target DNA can be ascertained, and a large number of PCRs can be screened for abnormal reaction conditions, all by comparing the actual growth rate of dsDNA during the PCR to the predicted growth curve for a particular DNA target in a thermal cycling apparatus.

In one form of the invention, there is provided a method for determining an unknown starting molar concentration of target nucleic acid molecules at the beginning of a polymerase chain reaction in a sample reaction mixture containing suitable buffers, two complementary kinds of oligonucleotide primers, a molar excess of four kinds of nucleoside triphosphates, a DNA polymerase, and said unknown starting molar concentration of target nucleic acid molecules, wherein the two kinds of primers are provided in a known concentration (Cpo), said method including the steps of adding a reporter molecule which does not significantly interfere with the reaction and does not emit a strong signal in the absence of double stranded DNA, but makes the dsDNA created by the reaction detectable and measureable at least once each cycle, and thermal cycling one or more standard rection mixtures which are substantially the same in every respect except they have known starting molar concentration of target nucleic acid molecules to obtain one or more growth curves with known starting molar concentrations of target nucleic acid molecules. The method further includes the steps of exciting the reaction mixture during at least the extension portion of each cycle, detecting and measuring the intensity of the signal during at least the extension portion of each of the cycles, converting the intensity to molar concentration values of dsDNA and storing the molar concentration values for each of the extension portions of the cycles, and generating a measured curve of molar concentration of dsDNA versus cycle number from the stored concentration values. The next steps are, using successive approximations, determining values of $e_v$, $e_s$, and a which provide a best fit of the measured curve to said one or more known growth curves according to the following relation:

$$C_{n+1} = C_n e_v \left\{ 1 + e_s \left( 1 + \frac{aC_n}{C_{po} - (C_n - C_o)} \right) \right\}$$

where:

$C_{n+1}$ -- and $C_n$ are the DNA template molar concentrations measured during the nth and n+1th cycle extension periods;

$e_v$ is in theory the template's probability of survival to the next cycle;

$e_s$ is in theory the template's probability of being synthesized;

$C_o$ is the molar concentration of starting target nucleic acid molecules;

$C_{po}$ is the starting primer molar concentration;

a is in theory the primer/complementary strand competition factor;

and then calculating the molar concentration of starting nucleic acid of the unknown samples by fixing $e_v$, $e_s$, and a, and adjusting the starting concentration $C_o$ to get a best fit to the measured growth curve of each unknown sample.

In another form of the invention, there is provided a method for determining an unknown starting molar concentration of target nucleic acid molecules at the beginning of a polymerase chain reaction in a sample reaction mixture containing suitable buffers, two complementary kinds of oligonucleotide primers, a molar excess of four kinds of nucleoside triphosphates, a DNA polymerase, and the unknown starting molar concentration of target nucleic acid molecules, wherein the two kinds of primers are provided in a known concentration ($C_{po}$), said method including the steps of adding a reporter molecule which does not significantly interfere with the reaction and does not emit a strong signal in the absence of double-stranded DNA, but makes the dsDNA created by the reaction detectable and measureable at least once each cycle, thermal cycling the reaction mixture for a number of cycles, each including at least denaturing and extension periods, sufficient to establish a desired final concentration of nucleic acid molecules, and exciting the reaction mixture during at least the extension portion of each cycle. The next steps include detecting and measuring the intensity of the signal during at least the extension portion of each of the cycles, converting the intensity to molar concentration values of dsDNA and storing the molar concentration values for each of the extension portions of each of the cycles, and generating a measured curve of molar concentration of dsDNA versus cycle number from the stored concentration values. Next, using successive approximations, determine values of $e_v$, $e_s$, a, $c_z(n)$ and $A_z(n)$ which provide a best fit of the measured curve to a theoretical curve according to the following relation:

$C_{n+1} = C_n e_v$ plus the minimum of $$\left[ \frac{C_n e_v e_s}{1 + \frac{aC_n}{C_{po} + C_o - C_n}} \right] \text{ or } \left[ \frac{C_z(n) A_z(n) t_x}{L_t - L_p} \right]$$

where:

$C_{n+1}$ and $C_n$ are the DNA template molar concentrations at the end of the n and n+1 cycle extension periods;

$e_v$ is in theory the template's probability of survival to the next cycle;

$e_s$ is in theory the template's probability of being synthesized;

$C_o$ is the molar concentration of starting target nucleic acid molecules;

$C_{po}$ is the starting primer molar concentration;

a is in theory the primer/complementary strand competition factor;

$C_z$ is molar concentration of the polymerase enzyme;

$A_z$ is specific activity of the polymerase ensyme;

$t_x$ is extension time in seconds;

$L_t$ is length of template in bases;

$L_p$ is length of primers in bases; and then calculating the molar concentration of starting nucleic acid at cycle n=0 by varying the values of $e_v$, $e_s$, a, $C_z(n)$ and $A_z(n)$ and Co to get a best fit of the curve equation to the measured growth curve of the unknown sample.

In still another form, the invention provides a method for determining an unknown starting molar concentration of target nucleic acid molecules at the beginning of a polymerase chain reaction in a sample reaction mixture containing suitable buffers, two complementary kinds of oligonucleotide primers, a molar excess of four kinds of nucleoside triphosphates, a DNA polymerase, and the unknown starting molar concentration of target nucleic acid molecules, wherein the two kinds of primers are provided in a known concentration ($C_{po}$), the method comprising the steps of adding a reporter molecule which does not significantly interfere with the raction and does not emit a strong signal in the absence of double stranded DNA, but makes the dsDNA created by the reaction detectable and measurable at least once each cycle, thermal cycling one or more standard reaction mixtures which are substantially the same in every respect except they have known starting molar concentration of target nucleic acid molecules to obtain one or more growth curves with known starting molar concentrations of target nucleic acid molecules, and exciting the reaction mixture during at least the extension portion of each cycle. The next steps include detecting and measuring the intensity of the signal during at least the extension portion of each of the cycles, converting the intensity to molar concentration values of dsDNA and storing the molar concentration values for each of the extension portions of each of the cycles, and generating a measured curve of molar concentration of dsDNA versus cycle number from the stored concentration values. Next, using successive approximations, determine values of $e_v$, $e_s$, a, $C_z(n)$ and $A_z(n)$ which provide a best fit of the measured curve to the one or more known growth curves according to the following relation:

$C_{n+1} = C_n e_v$ plus the minimum of $$\left[ \frac{C_n e_v e_s}{1 + \frac{aC_n}{C_{po} + C_o - C_n}} \right] \text{ or } \left[ \frac{C_z(n) A_z(n) t_x}{L_t - L_p} \right]$$

where:

$C_{n+1}$ and $C_n$ are the DNA template molar concentrations at the end of the n and n+1 cycle extension periods;

$e_v$ is in theory the template's probability of survival to the next cycle;

$e_s$ is in theory the template's probability of being synthesized;

$C_o$ is the molar concentration of starting target nucleic acid molecules;

$C_{po}$ is the starting primer molar concentration;

a is in theory the primer/complementary strand competition factor;

$C_z$ is molar concentration of the polymerase enzyme;

$A_z$ is specific activity of the polymerase;

$t_x$ is extension time in seconds;

$L_t$ is length of template in bases;

$L_p$ is length of primers in bases; and thereafter calculating the molar concentration of starting nucleic acid of the unknown samples by fixing $e_v$, $e_s$, a, $C_z(n)$, and $A_z(n)$, and adjusting the starting concentration $C_o$ to get a best fit to the measured growth curve of each unknown sample.

Further, according to a form of the invention, there is provided an automated apparatus for evaluating in real time the expected adequacy of a polymerase chain reaction in a reaction mixture containing suitable buffers, two complementary kinds of oligonucleotide primers, a molar excess of four kinds of nucleoside triphosphates, a DNA polymerase, and an unknown starting molar concentration of target nucleic acid molecules, wherein the two kinds of primers are provided in a known molar concentration ($C_{po}$), and at least one kind of the two kinds of primers or four kinds of nucleoside triphosphates are labeled with a reporter molecule which does not emit a strong signal in the absence of double-stranded DNA, but makes the dsDNA created by the reaction detectable and measurable at least once each cycle, said apparatus including a thermal cycler for thermal cycling one or more standard reaction mixtures which are substantially the same in every respect except they have known starting molar concentration of target nucleic acid molecules to obtain one or more growth curves with known starting molar concentrations of target nucleic acid molecules, a detection system including means for exciting the reaction mixture during at least the extension portion of each cycle and means for detecting and measuring the intensity of the signal during at least the extension portion of each of said cycles, a microcomputer connected to the detection system for receiving signals therefrom and for converting the intensity to molar concentration values of dsDNA in the mixture and storing the molar concentration values for each of the extension portions of each of the cycles, and a user interface connected to the computer and the thermal cycler for inputting user instructions and displaying results information. According to the invention, the computer includes means for generating a measured curve of molar concentration of dsDNA versus cycle number from the stored concentration values, means for using successive approximations to determine characteristic parameter values of $e_v$, $e_s$, and a which provide a best fit of the measured curve to said one or more known growth curves according to the following relation:

$$C_{n+1} = C_n e_v \left\{ 1 + e_s \left( 1 + \frac{aC_n}{C_{po} - (C_n - C_o)} \right) \right\}$$

where:

$C_{n+1}$ and $C_n$ are the DNA target molar concentrations measured during the nth and n+1th cycle extension periods;

$e_v$ is in theory the target's probability of survival to the next cycle;

$e_s$ is in theory the target's probability of being synthesized;

$C_o$ is the molar concentration of starting target nucleic acid molecules;

$C_{po}$ is the starting primer molar concentration;

a is in theory the primer/complementary strand competition factor, and means are provided for calculating the molar concentration of starting nucleic acid of the unknown samples by fixing $e_v$, $e_s$, and a, and adjusting the starting concentration $C_o$ to get a best fit to the measured growth curve of each unknown sample.

The invention is directed in another form thereof to an automated apparatus for evaluating in real time the expected adequacy of a polymerase chain reaction in a reaction mixture containing suitable buffers, two complementary kinds of oligonucleotide primers, a molar excess of four kinds of nucleoside triphosphates, a DNA polymerase, and an unknown starting molar concentration of target nucleic acid molecules, wherein the two kinds of primers are provided in a known molar concentration ($C_{po}$), and at least one kind of the two kinds of primers or four kinds of nucleoside triphosphates are labeled with a reporter molecule which does not emit a strong signal in the absence of double-stranded DNA, but makes the dsDNA created by the reaction detectable and measurable at least once each cycle, said apparatus including a thermal cycler for thermal cycling the reaction mixture for a predetermined number of cycles, each including at least denaturing and annealing/extension periods, sufficient to establish a desired final concentration of nucleic acid molecules in which the primers are exhausted, and a detection system including means for exciting the reaction mixture during at least the extension portion of each cycle and means for detecting and measuring the intensity of the signal during at least the extension portion of each of the cycles. In addition, the apparatus includes a microcomputer connected to the detection system for receiving signals therefrom and for converting the intensity to molar concentration values of dsDNA in the mixture and storing the molar concentration values for each of the extension portions of each of the cycles, a user interface connected to the computer and the thermal cycler for inputting user instructions to the computer and displaying results information. This computer includes means for generating a measured curve of molar concentration of dsDNA versus cycle number from said stored concentration values, means for using successive approximations to determine characteristic parameter values of $e_v$, $e_s$, a, $C_z(n)$ and $A_z(n)$ which provide a best fit of the measured curve to a theoretical model curve according to the following relation:

$C_{n+1} = C_n e_v$ plus the minimum of $$\left[ \frac{C_n e_v e_s}{1 + \frac{aC_n}{C_{po} + C_o - C_n}} \right] \text{ or } \left[ \frac{C_z(n) A_z(n) t_x}{L_t - L_p} \right]$$

where:

$C_{n+1}$ and $C_n$ are the DNA target molar concentrations measured during the nth and n+1th cycle extension periods;

$e_v$ is in theory the target's probability of survival to the next cycle;

$e_s$ is in theory the target's probability of being synthesized;

$C_o$ is the molar concentration of starting target nucleic acid molecules;

$C_z$ is molar concentration of the polymerase enzyme;

$A_z$ is specific activity of the polymerase enzyme;

$t_x$ is extension time in seconds;

$L_t$ is length of template in bases;

$L_p$ is length of primer in bases;

$C_{po}$ is the starting primer molar concentration;

a is in theory the primer/complementary strand competition factor.

and, in addition, means are provided for calculating the molar concentration of starting nucleic acid at cycle n=0 by varying the values of $e_v$, $e_s$, a, $C_z(n)$ and $A_z(n)$ and $C_o$ to get a best fit of the curve equation to the measured growth curve of the unknown sample.

As yet another embodiment, the invention is directed to an automated apparatus for evaluating in real time the expected adequacy of a polymerase chain reaction in a reaction mixture containing suitable buffers, two complementary kinds of oligonucleotide primers, a molar excess of four kinds of nucleoside triphosphates, a DNA polymerase, and an unknown starting molar concentration of target nucleic acid molecules, wherein the two kinds of primers are provided in a known molar concentration ($C_{po}$), and at least one kind of said two kinds of primers or four kinds of nucleoside triphosphates are labeled with a reporter molecule which does not emit a strong signal in the absence of double-stranded DNA, but makes the dsDNA created by the reaction detectable and measurable at least once each cycle, said apparatus including a thermal cycler for thermal cycling one or more standard reaction mixtures which are substantially the same in every respect except they have known starting molar concentration of target nucleic acid molecules to obtain one or more growth curves with known starting molar concentrations of target nucleic acid molecules, and a detection system including means for exciting the reaction mixture during at least the extension portion of each cycle and means for detecting and measuring the intensity of the signal during at least the extension portion of each of the cycles. The apparatus also includes a microcomputer connected to said detection system for receiving signals therefrom and for converting the intensity to molar concentration values of dsDNA in the mixture and storing the molar concentration values for each of the extension portions of each of the cycles, a user interface connected to the computer and the thermal cycler for inputting user instructions to the computer and displaying results information. The computer includes means for generating a measured curve of molar concentration of dsDNA versus cycle number from said stored concentration values, and means for using successive approximations to determine characteristic parameter values of $e_v$, $e_s$, a, $C_z(n)$ and $A_z(n)$ which provide a best fit of the measured curve to said one or more known growth curves according to the following relation:

$C_{n+1} = C_n e_v$ plus the minimum of $$\left[ \frac{C_n e_v e_s}{1 + \frac{aC_n}{C_{po} + C_o - C_n}} \right] \text{ or } \left[ \frac{C_z(n) A_z(n) t_x}{L_t - L_p} \right]$$

where:

$C_{n+1}$ and $C_n$ are the DNA target molar concentrations measured during the nth and n+1th cycle extension periods;

$e_v$ is the target's probability of survival to the next cycle;

$e_s$ is the target's probability of being synthesized;

$C_o$ is the molar concentration of starting target nucleic acid molecules;

$C_z$ is molar concentration of the polymerase enzyme;

$A_z$ is specific activity of the polymerase enzyme;

$t_x$ is extension time in seconds;

$L_t$ is length of template in bases;

$L_p$ is length of primer in bases;

$C_{po}$ is the starting primer molar concentration;

a is the primer/complementary strand competition factor; and in addition, means are provided for calculating the molar concentration of starting nucleic acid of the unknown samples by fixing $e_v$, $e_s$, a, $C_z(n)$ and $A_z(n)$ and adjusting the starting concentration $C_o$ to get a best fit to the measured growth curve of each unknown sample.

These and other objects, features and advantages of the invention will become more apparent from a reading of the following Detailed Description when taken in conjunction with the appended claims and accompanying drawings.

DESCRIPTION OF THE PREFERRED EMBODIMENTS OF THE INVENTION

According to a preferred embodiment of the invention, there is provided an automated method for determining an unknown starting molar concentration of target nucleic acid molecules at the beginning of a polymerase chain reaction in a sample reaction mixture containing suitable buffers, two complementary kinds of oligonucleotide primers, a molar excess of four kinds of nucleoside triphosphates, a DNA polymerase, and the unknown starting molar concentration of target nucleic acid molecules. This method does not involve the use of any standard of known concentration. The method should preferably be automatically carried out by an automated thermal cycling apparatus which includes a microprocessor coupled to a fluorescence detection device and conventionally programmed with a spreadsheet program such as Microsoft® Excel. The reaction mixture includes known volumes of buffers and a substantial molar excess of dNTPs. The two kinds of primers in the reaction mixture are specifically provided in a predetermined known molar concentration ($C_{po}$) so as to be exhausted during the final cycles of the PCR protocol. The method comprises the steps of:

a) labeling at least one kind of the two kinds of primers or four kinds of nucleoside triphosphates with a reporter molecule which, when incorporated into an extension product generated by said polymerase chain reaction, is capable of emitting a detectable signal when appropriately excited, that is adding a reporter molecule which does not significantly interfere with the reaction and does not emit a strong signal in the absence of double-stranded DNA, but makes the dsDNA created by the reaction detectable and measurable at least once each cycle;

b) thermal cycling the reaction mixture for a predetermined number of cycles, each cycle including at least denaturing and extension periods, sufficient to establish a desired final concentration of nucleic acid molecules;

c) exciting the reaction mixture during at least part of the extension portion of each cycle so that a signal is emitted by each of the reporter molecules bound to an extension product;

d) detecting and measuring the intensity of this signal during at least said part of the extension portion of each of said cycles;

e) converting the intensity signal in a microprocessor to a molar concentration value of dsDNA and storing the molar concentration value for each of said extension portions of each of said cycles in a memory;

f) generating a measured curve of molar concentration of dsDNA versus cycle number in said microprocessor from said stored concentration values in said memory;

g) by using a successive approximation method in a spreadsheet program in said microprocessor, determining values of $e_v$, $e_s$, $C_o$ and a which provide a best fit of the measured curve to the following relation:

$$C_{n+1} = C_n e_v \left\{ 1 + e_s \left( 1 + \frac{aC_n}{C_{po} - (C_n - C_o)} \right) \right\}$$

wherein:

n is the nth cycle number in the PCR;

$C_{n+1}$ and $C_n$ are the DNA template molar concentrations measured during the nth and nth+1 cycle extension periods;

$e_v$ is in theory the template's probability of survival to the next cycle;

$e_s$ is in theory the template's probability of being synthesized;

$C_o$ is the molar concentration of starting target nucleic acid molecules;

$C_{po}$ is the starting primer molar concentration;

a is the primer/complementary strand competition factor.

h) displaying the molar concentration of starting nucleic acid molecules at cycle n=0 ($C_o$).

Figure 4:
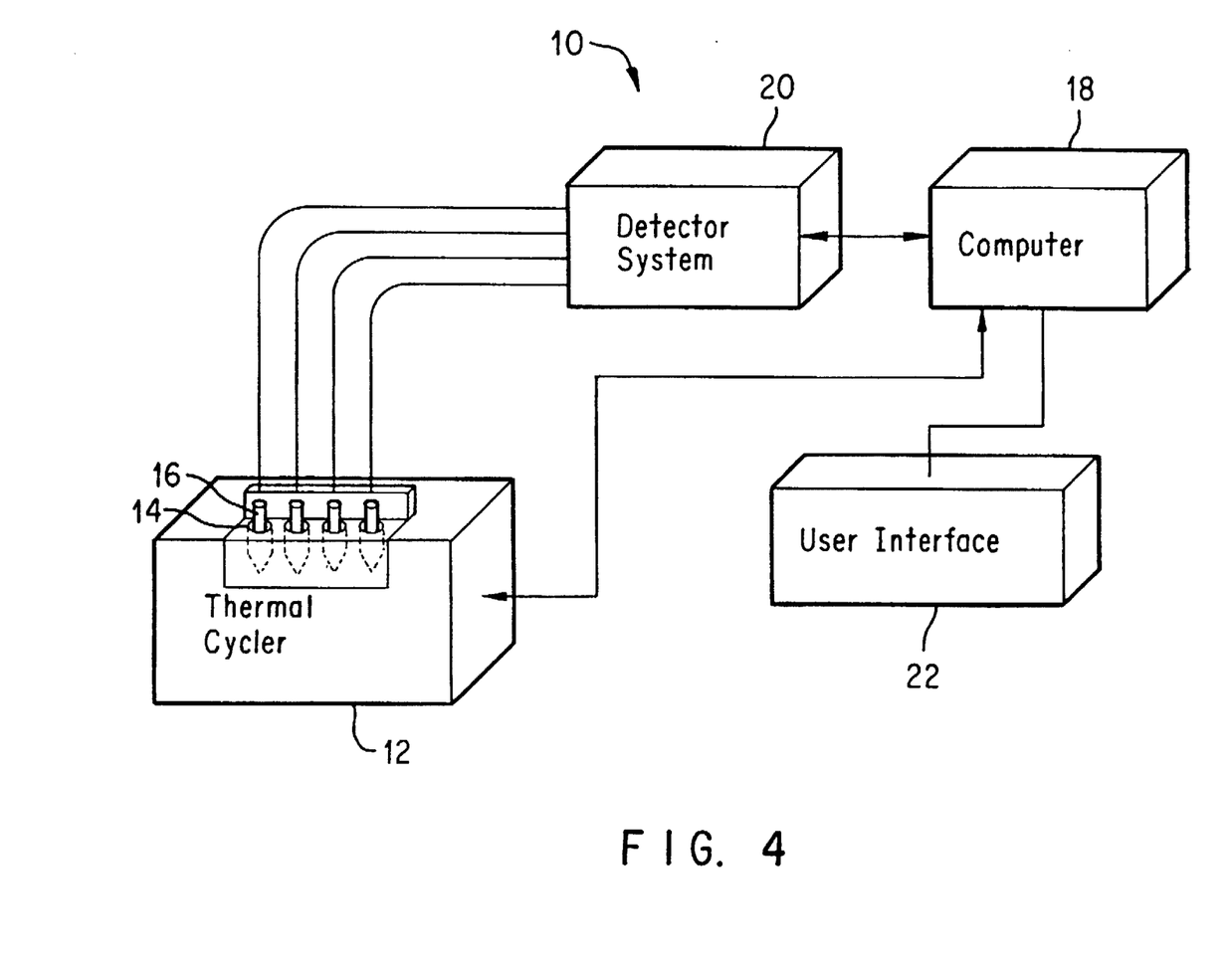
FIG. 4 is a simplified block diagram of the apparatus in accordance with the invention.

The apparatus in accordance with the invention is shown as a block diagram in FIG. 4. The apparatus 10 comprises a computer controlled thermal cycler 12 containing a plurality of wells 14 for holding a plurality of tubes 16 containing PCR reaction mixes, a microcomputer 18, a detection system 20 coupled to the wells 14 in the thermal cycler 12 and to the microcomputer 18, and a user interface 22 between the thermal cycler 12, the detection system 20, and the microcomputer 18.

The thermal cycler 12 may be of conventional design such as the System 9600 by The Perkin-Elmer Corporation which can hold up to 96 reaction mix samples in sample tubes in the wells 14 of its thermal cycling block. The tubes 16 are typically polypropylene tubes with transparent caps. The lid of the thermal cycler over the tubes is particularly adapted to receive and support the input devices of the detection system.

The detection system 20, in the case of a fluorescence labeling scheme, preferably may consist of a light source, fiber optic connectors and light tubes connected between the top of the wells and a CCD array, and suitable signal amplification and conversion circuitry for converting light signals to a digital input to the computer, or it may be a digital camera system such as was used and described in the Higuchi et al paper. The output of the detection system is fed to the computer 18 for data storage and manipulation.

The detector system is preferably a multiplexed fluorimeter containing an excitation light source, which may be a visible light laser or an ultraviolet lamp, a multiplexer device for distributing the excitation light to the individual reaction tubes 16 through the fiber optic tubes and connectors and for receiving fluorescent light from the reaction tubes 16, a filtering means for separating the fluorescence light from the excitation light by their wavelengths, and a detection means for measuring the fluorescence light intensity. The fluorescence originates from an intercalating dye such as ethidium bromide which fluoresces strongly in the presence of double stranded DNA. The fluorescence from each PCR is measured at the end of each extension portion of each thermal cycle. The signals are processed in the computer 18 to measure the molar concentration of dsDNA present in each sample tube 16. The series of DNA concentrations thus measured for each reaction tube during each extension portion of each PCR cycle is stored in the computer 18. The measured values versus cycle number constitutes the growth curve for the PCR in each sample tube 16.

The computer 18 and user interface 22 may be a single dedicated device or may be a conventional commercially available personal computer (PC) system with a keyboard and video monitor. The computer 18 and user interface are used for display of growth curve data, inputting the instructions to the spreadsheet program in the computer, manipulating growth curve data, and displaying the PCR results as well as providing the necessary thermal cycler controls. The computer 18 performs a multi-variable least squares curve fitting process to determine the characteristic parameters for each of the PCRs that give the best fit to the model equation.

Thus, it will be appreciated that the real time monitoring of DNA during thermal cycling in accordance with the present invention makes it possible to predict the molar concentration of starting copies of the target or template DNA even though the primer concentration may have been run to exhaustion or the exponential amplification process may not have been continued to completion. It has been found that the shape of the growth curve of dsDNA product during a PCR process is uniquely determined by the model equation:

$$C_{n+1} = C_n e_v \left\{ 1 + e_s \left( 1 + \frac{aC_n}{C_{po} - (C_n - C_o)} \right) \right\}$$

where:

$C_{n+1}$ and $C_n$ are the DNA template molar concentrations measured during the n and n+1 cycle extension periods;

$e_v$ is the template's probability of survival to the next cycle;

$e_s$ is the template's probability of being synthesized;

$C_o$ is the molar concentration of starting target nucleic acid molecules;

$C_{po}$ is the starting primer molar concentration; and a is the primer/complementary strand competition factor.

The growth curve of concentration versus cycle number in accordance with this equation is a unique curve. There is only one combination of characteristic parameters $e_s$, $e_v$, a, and $C_o$ which fit the above equation to the measured values of the actual growth curve for a particular PCR.

Figure 1:
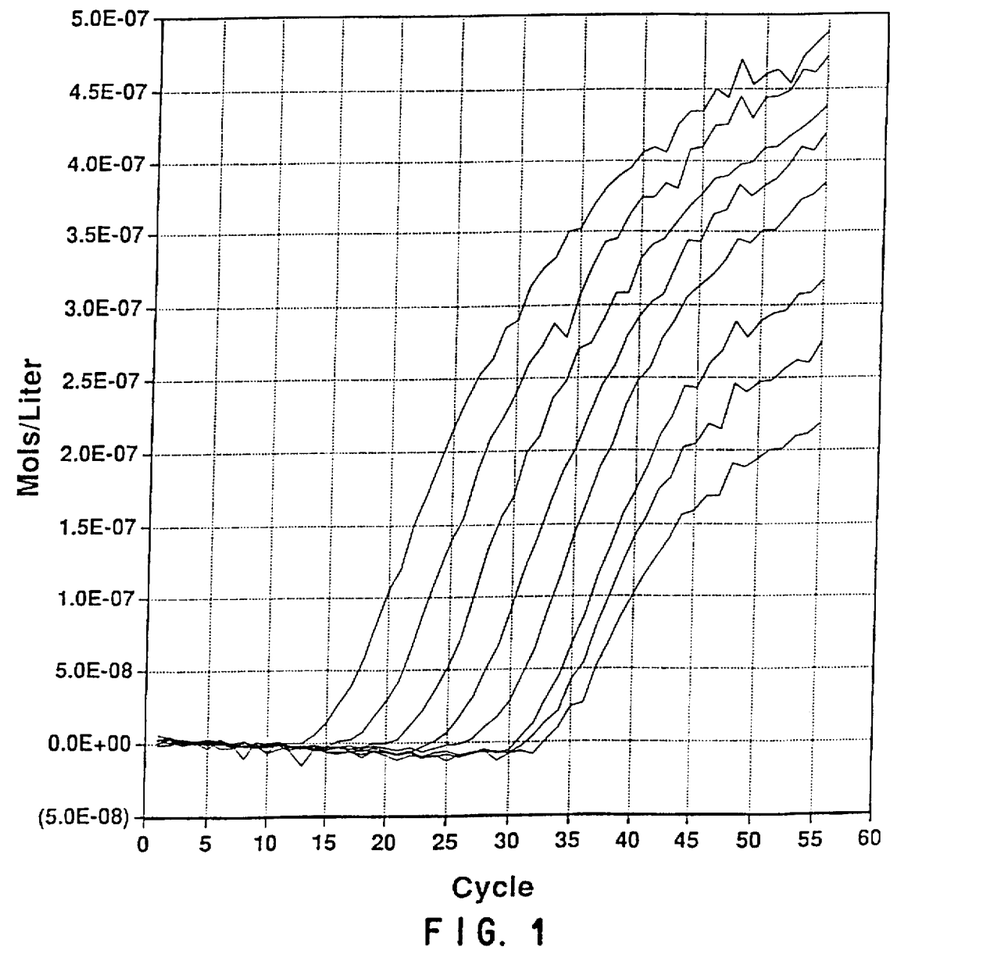
FIG. 1 is a graph of fluorescence versus cycle number for the data taken from the Higuchi et al paper.
Figure 2:
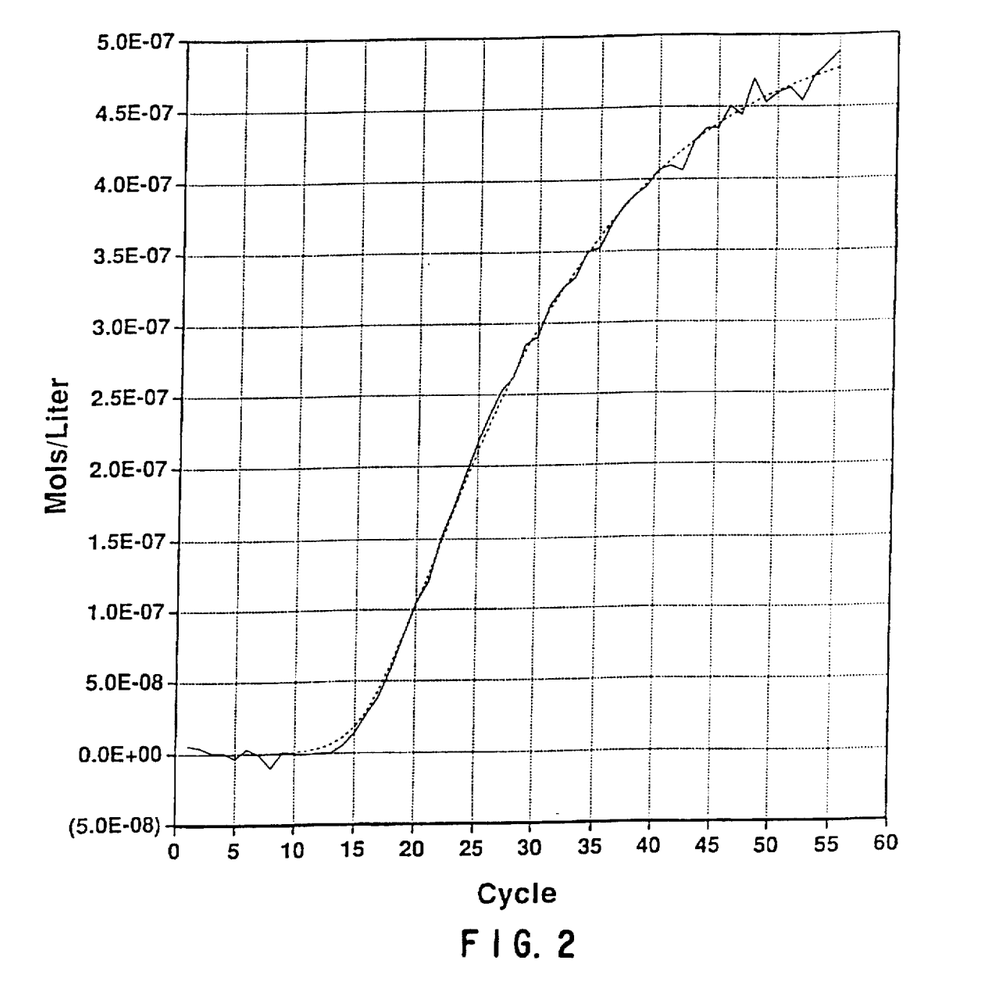
FIG. 2 is a graph of concentration versus cycle number for one of the curves shown in FIG. 1 in which $10^8$ HIV ssDNA per 100 µL starting copies were present.

The parameter $e_s$ can be viewed as a measure of the efficiency of synthesis of a given template ssDNA into dsDNA. The parameter $e_v$ can be viewed as a measure of the efficiency of survival of a template ssDNA from one cycle to the next cycle. These two parameters primarily describe the shape or slope of the exponential portion of the growth curve (which appears as a straight line portion of the growth curve shown in FIG. 2).

The upper curved portion of the growth curve is described by the term a which represents a measure of competition between the primers and the complementary strands for annealing to a given target DNA segment. The shape or curvature of this upper portion will be a very gradual curve if there is a substantial excess of both primers and enzyme. However, if primer concentration is limited so as to become exhausted, as in primer limited PCR, the curve portion will have the same shape but will reach its horizontal asymptote indicative of the concentration of final product and primer exhaustion.

There are a number of useful applications to which this invention may be applied. For example, it is not necessary for the measured PCR to be carried out to completion, e.g. exhaustion of at least one reagent in the mixture. It is merely necessary for a significant number of cycles to be performed so that amplification above the level of nonspecific signal background is achieved and the values of the characteristic parameters can be determined.

The successive approximations used by a conventional spreadsheet program such as the "solver" formula in Microsoft Excel are particularly suited for, and are used in solving the equation for this unique set of characteristic parameters. When there is insufficient enzyme activity to complete the synthesis of all primed single strands formed during the anneal/extend times, the growth curve becomes enzyme limited.

The primer-limited activity discussed hereinbefore can be extended to include the effects of enzyme limitation on the growth curve.

This is done by running a parallel caluclation each cycle to find the maximum possible number of bases that can be polymerized by the enzyme activity present at that cycle.

From the known initial enzyme activity in "Units", calculate the initial molar concentration, $C_{zo}$. For Taq polymerase $C_{zo}=3.55\times10^{-10}$ (mol/liter)/(Unit/100 µL). Cz may decline with increased cycles.

The specific activity of the polymerase, $A_z$, in mols of bases synthesized per second per mol of enzyme varies with temperature, $Mg^{2+}$, and the reaction product phyrophosphate $P_2O_7^{4-}$.

In this case, it is assumed that enzyme molarity $C_z$ does not change significantly, but that specific activity is inhibited exponentially by buildup of pyrophosphate. Thus, $$A_z(n) = A_{max}\, e^{\frac{-[P_2O_7]}{k_i}}$$

where $A_{max}$ is the uninhibited specific activity $k_i$ is the concentration of $[P_2O_7]$ which cuts activity to $A^{max}e^{-1}$ This results in 1 pyrophosphate for each base polymerized, so for double-stranded molarity $C_n$:

$$[P_2O_7]=2(C_n-C_o)(L_t-L_p).$$

Using an assumption about how $A_z(n)$ varies with n, the maximum possible growth of template molarity at the nth cycle is $$C_{nmax} = \frac{Cz(n)Az(n)tx}{L_t-L_p}$$

Here $t_x$ is extension time in seconds $L_t$ is length of template in bases $L_p$ is length of primers in bases In order to add the enzyme limitation to the primer limited PCR discussed hereinbefore the increment each cycle is the lesser of the primer or the enzyme limit. The calculation of $C_{n+1}$ is changed to:
$C_{n1}=C_{nev}$ plus the minimum of $$\left[\frac{C_n e_\nu e_s}{1+\frac{aC_n}{C_{po}+C_o-C_n}}\right] \text{ or } \left[\frac{Cz(n)Az(n)t_x}{L_t-L_p}\right]$$

The following examples illustrate the application of the present invention to the PCR process.

EXAMPLE

The raw data from Higuchi et al's paper, for $10^8$ starting copies of HIV ssDNA per 100 µL, was converted to Moles per liter and plotted versus cycle number. The results are graphically represented by the solid line shown in FIG. 2. The data was also entered into a computer and compared via the Excel spreadsheet with the theoretical equation to establish best fit values of $e_s$, $e_\nu$, and a when $C_o$ was set to the known molar concentration corresponding to $10^8$ copies in the 100 µL reaction volume. The resultant curve is shown as the dotted line in FIG. 2.

Figure 3:
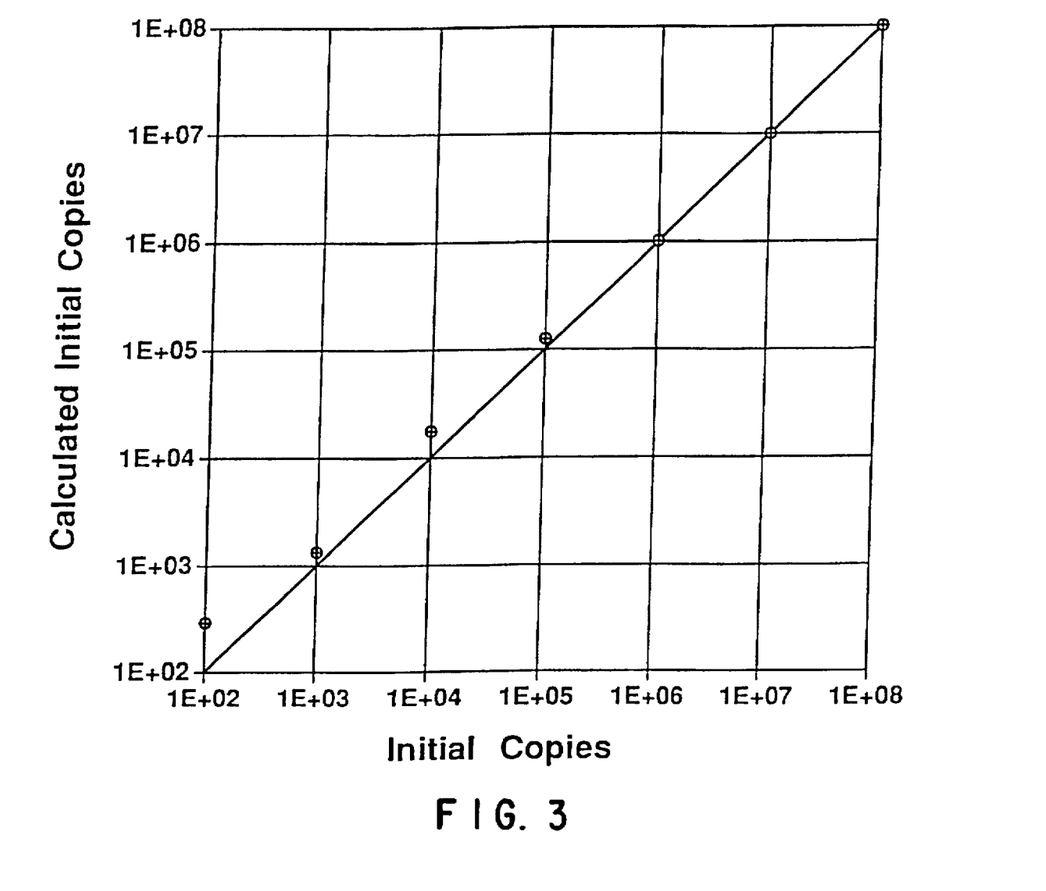
FIG. 3 is a graph of calculated starting copies versus actual starting copy for the Higuchi et al data, calculated by the method of this invention.

FIG. 3 is a graph of the calculated initial copies versus known initial copies. It is based on only one set of $e_s$, $e_\nu$, and a values determined by the best fit of the equation set forth above to the Higuchi et al data for $10^8$ starting copies as the only standard. These characteristic parameters $e_s$, $e_\nu$, and a were fixed in the equation. The equation was then used in the Excel spreadsheet to determine the calculated initial copies by varying $C_o$ alone to get a best fit to each of the five other sets of Higuchi et al growth data. FIG. 3 shows that there is a very close agreement, virtually 1 to 1, between the actual known initial copies and the calculated initial copy values according to the equation, except for the low calculated copy number at $10^2$ initial copies. This is most likely due to there being a significant additional non-specific reaction creating more DNA than the specific reaction alone would have created.

It must be noted that the molarity of the PCR product must be ascertainable for the model relationship to hold. Thus the fluorescence measured must be convertible to moles per liter of reagent mixture. It is not necessary to use fluorescence to detect and measure the concentration of product. Fluorescence was simply the technique applied here. Any observable technique and non-destructively measurable phenomenon may be used.

The growth curve shape parameters can be applied in several ways. Accurate quantitation of starting copy number using a standard of known concentration is possible, as described above. If a sample of target DNA template with known concentration is available it may be used in a primer limited PCR to obtain one or more growth curves. First, perform the PCR with the known starting template and primer concentrations to obtain one or more model growth curves. Then fit the data of the primer limited model curves to the equation for the growth curves using the known starting template and primer concentrations and determine the best fit values for the three characteristic parameters $e_s$, $e_\nu$, and a. Then run PCRs under identical conditions with samples of unknown starting concentrations of template and record the growth curve data. Fixing the three characteristic parameters just determined with the standard, determine the starting template concentration of each unknown sample as that value that makes the calculated growth curve a best fit to the measured growth curve data. Using this method, the starting concentration can be more accurately determined compared to the Higuchi et al methodology. This is because all of the growth curve data are utilized rather than one or a few points along the growth curve.

Estimation of starting concentration of a template without any standard of known concentration is also possible. When no standard of known template concentration is available, first run a primer limited PCR with the unknown and record its growth curve. Then, fixing only the known starting primer concentration, vary the growth curve shape parameters (the characteristic parameters $e_s$, $e_\nu$, and a) together with the starting template concentration $C_o$ to obtain a four parameter best fit to the measured growth curve data. In most applications, a fit can be obtained that gives a usefully accurate value for the starting template concentration, as well as values for the other characteristic parameters.

It is surprising that this works. However, the reason that it works for most applications is that in a normal primer limited PCR, the shape of the growth curve is so constrained by the amplification process that there exists no large range of starting template concentrations that will give a reasonable fit to a measured curve.

Screening of large numbers of PCRs for abnormal reaction conditions is also possible. Typically, a thermal cycler combined with real time detection and monitoring can simultaneously perform as many as 96 PCRs These PCRs will all be identical PCR systems run under identical conditions with only the starting template concentration being an unknown variable in each reaction. In addition, some of the samples may be known concentration control standards.

All of these simultaneously run PCRs should have growth curves of substantially the same shape. In other words, when the data is best fit to the equation, the values of the characteristic parameters $e_s$, $e_v$, and a determined are almost identical. However, if among them there are some in which a non-specific reaction has started, or in which an inhibiting contaminant has been introduced, or in which reaction conditions depart significantly from the norm, these will, in most applications, have measured growth curves of significantly different shape and hence different characteristic parameters, regardless of the starting concentration of target.

It is a computational process on the measured data for the apparatus which includes a computer controlled thermal cycler with real time detection capability to measure and record the growth curve for each PCR sample and determine its characteristic parameters. If, in any sample, any of the parameters depart significantly from the known norm for the PCR, or if it is impossible to get a good quality fit with any set of parameters, it is a warning that the measurement of that sample may be unreliable. A good quality fit is one where the root mean square error of fit is comparable to the known noise of measurement.

For example, a value for $e_s$ should be about 1.0. A value of $e_s$ significantly greater than 1.0 indicates that a parallel non-specific amplification reaction may be underway. An abnormal value of a may indicate incorrect cycling temperatures or reagent concentrations. A value of $e_v$ much lower than 1.0 may indicate the presence of an inhibitor. And if the RMS error of the best fit is 5 times the known measurement noise, there is very likely to be something wrong with that PCR or measurement.

Conversely, if the quality of the fit of the equation to the measured growth curve is good, with the root mean square error not much greater than the known error of measurement of the detection system, and the characteristic parameters are close to their expected norms, this is strong evidence that the measurement of each such PCR is reliable and probably specific.

In one preferred form of the invention, there is provided an automated apparatus for evaluating in real time the expected adequacy of a polymerase chain reaction in a reaction mixture containing suitable buffers, two complementary kinds of oligonucleotide primers, a molar excess of four kinds of nucleoside triphosphates, a DNA polymerase, and an unknown starting molar concentration of target nucleic acid molecules, wherein said two kinds of primers are provided in a known molar concentration ($C_{po}$), and at least one kind of said two kinds of primers or four kinds of nucleoside triphosphates are labeled with a reporter molecule which does not emit a strong signal in the absence of double-stranded DNA, but makes the dsDNA created by the reaction detectable and measurable at least once each cycle, said apparatus comprising:

a) a thermal cycler for thermal cycling one or more standard reaction mixtures which are substantially the same in every respect except they have known starting molar concentration of target nucleic acid molecules to obtain one or more growth curves with known starting molar concentrations of target nucleic acid molecules;

b) a detection system including means for exciting said reaction mixture during at least the extension portion of each cycle and means for detecting and measuring the intensity of said signal during at least the extension portion of each of said cycles;

c) a microcomputer connected to said detection system for receiving signals therefrom and for converting said intensity to molar concentration values of dsDNA in said mixture and storing said molar concentration values for each of said extension portions of each of said cycles;

d) a user interface connected to said computer and said thermal cycler for inputting user instructions to said computer and displaying results information;

wherein said computer includes:

i) means for generating a measured curve of molar concentration of dsDNA versus cycle number from said stored concentration values;

ii) means for using successive approximations to determine characteristic parameter values of $e_v$, $e_s$, and a which provide a best fit of the measured curve to said one or more known growth curves according to the following relation: $C_{n+}=C_{ne_v}$ plus the minimum of $$\left[ \frac{C_n e_v e_s}{1 + \frac{aC_n}{C_{po} + C_o - C_n}} \right] \text{ or } \left[ \frac{C_z(n)Az(n)t_x}{L_t - L_p} \right]$$

where:

$C_{n+1}$ and $C_n$ are the DNA target molar concentrations measured during the nth and n+1th cycle extension periods;

$e_v$ is the target's probability of survival to the next cycle;

$e_s$ is the target's probability of being synthesized;

$C_o$ is the molar concentration of starting target nucleic acid molecules;

$C_z$ is molar concentration of the polymerase enzyme;

$A_z$ is specific activity of the polymerase enzyme;

$t_x$ is extension time in seconds;

$L_t$ is length of template in bases;

$L_p$ is length of primer in bases;

$C_{po}$ is the starting primer molar concentration;

a is the primer/complementary strand competition factor.

iii) means for calculating the molar concentration of starting nucleic acid of the unknown samples by fixing $e_v$, $e_s$, a, $C_z(n)$ and $A_z(n)$ and adjusting the starting concentration $C_o$ to get a best fit to the measured growth curve of each unknown sample.

It will thus be seen that the present invention does indeed provide new and improved method and apparatus for quantitative analysis of nucleic acid samples such as DNA in a polymerase chain reaction (PCR) process.

Although certain particular embodiments of the invention are herein disclosed for purposes of explanation, further modification thereof, after study of this specification, will be apparent to those skilled in the art to which the invention pertains. Reference should accordingly be had to the appended claims in determining the scope of the invention.

What is claimed is:

1. A method for determining an unknown starting molar concentration of target nucleic acid molecules at the begin-

19 ning of a polymerase chain reaction in a sample reaction mixture containing suitable buffers, two complementary oligonucleotide primers, a molar excess of four nucleoside triphosphates, a DNA polymerase, and said unknown starting molar concentration of target nucleic acid molecules, wherein said two primers are provided in a known concentration ($C_{po}$), said method comprising the steps of:

a) adding to the reaction mixture a reporter molecule which does not emit a strong signal in the absence of double-stranded DNA, but makes the dsDNA created by the reaction detectable and measurable at least once each cycle;

b) thermal cycling said reaction mixture for a predetermined number of cycles, each including at least denaturing and extension periods, sufficient to establish a desired final concentration of nucleic acid molecules;

c) exciting said reaction mixture of step b) during at least the extension period of each cycle;

d) detecting and measuring the intensity of said signal during at least the extension portion of each of said cycles;

e) converting said intensity to corresponding molar concentration values of dsDNA and storing said molar concentration values for each of said extension portions of each of said cycles;

f) generating a measured curve of molar concentration of dsDNA versus cycle number from said stored concentration values;

g) using successive approximations, determine values of $e_v$, $e_s$, and a which provide a best fit of the measured curve to a theoretical curve according to the following theoretical relation:

$$C_{n+1} = C_n e_v \left\{ 1 + e_s \left( 1 + \frac{aC_n}{C_{po} - (C_n - C_o)} \right) \right\}$$

where:

$C_{n+1}$ and $C_n$ are the DNA template molar concentrations measured during the n and n+1 cycle extension periods;

$e_v$ is the template's probability of survival to the next cycle;

$e_s$ is the template's probability of being synthesized;

$C_o$ is the molar concentration of starting target nucleic acid molecules;

$C_{po}$ is the starting primer molar concentration;

a is the primer/complementary strand competition factor; and h) calculating the molar concentration of starting nucleic acid at cycle n=0 by varying the values of $e_v$, $e_s$, a, and $C_o$ to get a best fit of the curve equation of step g) to the measured growth of the unknown sample, thereby determining said unknown starting molar concentration of said target nucleic acid molecules.

2. A method for determining an unknown starting molar concentration of target nucleic acid molecules at the beginning of a polymerase chain reaction in a sample reaction mixture containing suitable buffers, two complementary oligonucleotide primers, a molar excess of four nucleoside triphosphates, a DNA polymerase, and said unknown starting molar concentration of target nucleic acid molecules, wherein said two primers are provided in a known molar concentration ($C_{po}$), said method comprising the steps of:

a) adding to the reaction mixture a reporter molecule which does not emit a strong signal in the absence of

20 double-stranded DNA, but makes the dsDNA created by the reaction detectable and measurable at least once each cycle;

b) thermal cycling said reaction mixture for a predetermined number of cycles, each including at least denaturing and extension periods, sufficient to establish a desired final concentration of nucleic acid molecules in which said primers are exhausted;

c) exciting said reaction mixture of step b) during at least the extension period of each cycle;

d) detecting and measuring the intensity of said signal during at least the extension portion of each of said cycles;

e) converting said intensity to molar concentration values of dsDNA in said mixture of step b) and storing said molar concentration values for each of said extension portions of each of said cycles;

f) generating a measured curve of molar concentration of dsDNA versus cycle number from said stored concentration values;

g) using successive approximations, determining values of $e_v$, $e_s$, and a which provide a best fit of the measured curve to a theoretical curve according to the following theoretical relation:

$$C_{n+1} = C_n e_v \left\{ 1 + e_s \left( 1 + \frac{aC_n}{C_{po} - (C_n - C_o)} \right) \right\}$$

where:

$C_{n+1}$ and $C_n$ are the DNA target molar concentrations measured during the nth and n+1th cycle extension periods;

$e_v$ is the target's probability of survival to the next cycle;

$e_s$ is the target's probability of being synthesized;

$C_o$ is the molar concentration of starting target nucleic acid molecules;

$C_{po}$ is the starting primer molar concentration;

a is the primer/complementary strand competition factor; and h) calculating the molar concentration of starting nucleic acid at cycle n=0 by varying the values of $e_v$, $e_s$, a, and $C_o$ to get a best fit of the curve equation of step g) to the measured growth curve of the unknown sample, thereby determining said unknown starting molar concentration of said target nucleic acid molecules.

3. A method for determining an unknown starting molar concentration of target nucleic acid molecules at the beginning of a polymerase chain reaction in a sample reaction mixture containing suitable buffers, two complementary oligonucleotide primers, a molar excess of four nucleoside triphosphates, a DNA polymerase, and said unknown starting molar concentration of target nucleic acid molecules, wherein said two primers are provided in a known concentration (Cpo), said method comprising the steps of:

a) adding to the reaction mixture a reporter molecule which does not emit a strong signal in the absence of double stranded DNA, but makes the dsDNA created by the reaction detectable and measurable at least once each cycle;

b) thermal cycling one or more standard reaction mixtures which have known starting molar concentration of target nucleic acid molecules to obtain one or more growth curves with known starting molar concentrations of target nucleic acid molecules;

c) exciting said reaction mixture during at least an extension portion of each cycle;
d) detecting and measuring the intensity of said signal during at least the extension portion of each of said cycles;
e) converting said intensity to molar concentration values of dsDNA and storing said molar concentration values for each of said extension portions of said cycles;
f) generating a measured curve of molar concentration of dsDNA versus cycle number from said stored concentration values;
g) using successive approximations, determining values of $e_v$, $e_s$, and a which provide a best fit of the measured curve to said one or more known growth curves according to the following relation:

$$C_{n+1} = C_n e_v \left\{ 1 + e_s / \left( 1 + \frac{aC_n}{C_{po} - (C_n - C_o)} \right) \right\}$$

where:

$C_{n+1}$ and $C_n$ are the DNA template molar concentrations measured during the n and n+1 cycle extension periods where n=1,2,3, . . . ;

$e_v$ is in theory the template's probability of survival to the next cycle;

$e_s$ is in theory the template's probability of being synthesized;

$C_o$ is the molar concentration of staring target nucleic acid molecules;

$C_{po}$ is the starting primer molar concentration;

a is in theory the primer/complementary strand competition factor; and h) calculating the molar concentration of starting nucleic acid of the unknown samples by selecting values for $e_v$, $e_s$, and a, and adjusting the starting concentration $C_o$ to get a best fit to the measured growth curve of each unknown sample, thereby determining said unknown starting molar concentration of said target nucleic acid molecules.

4. A method for determining an unknown starting molar concentration of target nucleic acid molecules at the beginning of a polymerase chain reaction in a sample reaction mixture containing suitable buffers, two complementary oligonucleotide primers, a molar excess of four nucleoside triphosphates, a DNA polymerase, and said unknown starting molar concentration of target nucleic acid molecules, wherein said two primers are provided in a known concentration ($C_{po}$), said method comprising the steps of:

a) adding to the reaction mixture a reporter molecule which does not emit a strong signal in the absence of double stranded DNA, but makes the dsDNA created by the reaction detectable and measurable at least once each cycle;
b) thermal cycling said reaction mixture for a number of cycles, each including at least denaturing and extension periods, sufficient to establish a desired final concentration of nucleic acid molecules;
c) exciting said reaction mixture during at least the extension period of each cycle;
d) detecting and measuring the intensity of said signal during at least the extension portion of each of said cycles;
e) converting said intensity to molar concentration values of dsDNA and storing said molar concentration values for each of said extension portions of each of said cycles;

f) generating a measured curve of molar concentration of dsDNA versus cycle number from said stored concentration values;
g) using successive approximations, determining values of $e_v$, $e_s$, a, $C_z(n)$ and $A_z(n)$ which provide a best fit of the measured curve to a theoretical curve according to the following relation:

$C_{n+1} = C_n e_v$ plus the minimum of $$\left[ \frac{C_n e_v e_s}{1 + \frac{aC_n}{C_{po} + C_o - C_n}} \right] \text{ or } \left[ \frac{C_z(n) A_z(n) t_x}{L_t - L_p} \right]$$

where:

$C_{n+1}$ and $C_n$ are the DNA template molar concentrations at the end of the nth and n+1th cycle extension periods;

$e_v$ is in theory the template's probability of survival to the next cycle;

$e_s$ is in theory the template's probability of being synthesized;

$C_o$ is the molar concentration of starting target nucleic acid molecules;

$C_{po}$ is the starting primer molar concentration;

a is in theory the primer/complementary strand competition factor;

$C_z$ is molar concentration of the polymerase enzyme;

$A_z$ is specific activity of the polymerase enzyme;

$t_x$ is extension time in seconds;

$L_t$ is length of template in bases;

$L_p$ is length of primers in bases; and h) calculating the molar concentration of starting nucleic acid at cycle n=0 by varying the values of $e_v$, $e_s$, a, $C_z(n)$ and $A_z(n)$ and $C_o$ to get a best fit of the curve equation of step g) to the measured growth curve of the unknown sample, thereby determining said unknown starting molar concentration of said target nucleic acid molecules.

5. A method for determining an unknown starting molar concentration of target nucleic acid molecules at the beginning of a polymerase chain reaction in a sample reaction mixture containing suitable buffers, two complementary oligonucleotide primers, a molar excess of four nucleoside triphosphates, a DNA polymerase, and said unknown starting molar concentration of target nucleic acid molecules, wherein said two primers are provided in a known concentration ($C_{po}$), said method comprising the steps of:

a adding to the reaction mixture a reporter molecule which does not emit a strong signal in the absence of double stranded DNA, but makes the dsDNA created by the reaction detectable and measurable at least once each cycle;
b) thermal cycling one or more standard mixtures which are substantially the same in every respect except they have known starting molar concentration of target nucleic acid molecules to obtain one or more growth curves with known starting molar concentrations of target nucleic acid molecules;
c) exciting said reaction mixture during at least an extension portion of each cycle;
d) detecting and measuring the intensity of said signal during at least the extension portion of each of said cycles;
e) converting said intensity to molar concentration values of dsDNA and storing said molar concentration values for each of said extension portions of each of said cycles;

f) generating a measured curve of molar concentration of dsDNA versus cycle number from said stored concentration values;

g) using successive approximations, determining values of $e_v$, $e_s$, a, $C_z(n)$ and $A_z(n)$ which provide a best fit of the measured curve to said one or more known growth curves according the following relation:

$C_{n+1} = C_n e_v$ plus the minimum of $$\left[ \frac{C_n e_v e_s}{1 + \frac{aC_n}{C_{po} + C_o - C_n}} \right] \text{ or } \left[ \frac{C_z(n)A_z(n)t_x}{L_t - L_p} \right]$$

where:
- $C_{n+1}$ and $C_n$ are the DNA template molar concentrations at the end of the nth and n+1th cycle extension periods where n=1,2,3 . . . ;
- $e_v$ is in theory the template's probability of survival to the next cycle;
- $e_s$ is in theory the template's probability of being synthesized;
- $C_o$ is the molar concentration of starting target nucleic acid molecules;
- $C_{po}$ is the starting primer molar concentration;
- a is in theory the primer/complementary strand competition factor;
- $C_z$ is molar concentration of the polymerase enzyme;
- $A_z$ is specific activity of the polymerase enzyme;
- $t_x$ is extension time in seconds;
- $L_t$ is length of template in bases;
- $L_p$ is length of primers in bases; and h) calculating the molar concentration of starting nucleic acid of the unknown samples by selecting values for $e_v$, $e_s$, a, $C_z(n)$ and $A_z(n)$ and adjusting the starting concentration $C_o$ to get a best fit to the measured growth curve of each unknown sample, thereby determining said unknown starting molar concentration of said target nucleic acid molecules.

* * * * *